US00RE50800E

(19) United States
(12) Reissued Patent
Indradas et al.

(10) Patent Number: US RE50,800 E
(45) Date of Reissued Patent: Feb. 17, 2026

(54) PRO-FRAGRANCE COMPOUNDS

(71) Applicant: FIRMENICH SA, Satigny (CH)

(72) Inventors: Brinda Indradas, Plainsboro, NJ (US); Gary B. Womack, Plainsboro, NJ (US)

(73) Assignee: FIRMENICH SA, Satigny (CH)

(21) Appl. No.: 17/903,659

(22) Filed: Sep. 6, 2022

Related U.S. Patent Documents

Reissue of:
(64) Patent No.: 10,767,136
Issued: Sep. 8, 2020
Appl. No.: 15/351,175
Filed: Nov. 14, 2016

U.S. Applications:
(60) Provisional application No. 62/255,361, filed on Nov. 13, 2015.

(51) Int. Cl.
*C11B 9/00* (2006.01)
*C07C 43/23* (2006.01)

(52) U.S. Cl.
CPC ..... *C11B 9/0061* (2013.01); *C07C 43/23* (2013.01)

(58) Field of Classification Search
None
See application file for complete search history.

(56) References Cited

U.S. PATENT DOCUMENTS

| | | | | |
|---|---|---|---|---|
| 6,165,953 | A * | 12/2000 | Gardlik | C11D 17/047 510/107 |
| 9,718,753 | B2 * | 8/2017 | Indradas | C11B 9/0003 |
| 2008/0319088 | A1 * | 12/2008 | Smith | C07C 45/49 514/693 |
| 2012/0129818 | A1 * | 5/2012 | Rajagopal | A61K 31/357 514/158 |
| 2017/0283737 | A1 * | 10/2017 | Indradas | C11B 9/0061 |
| 2018/0016521 | A1 * | 1/2018 | Indradas | C11B 9/0061 |

FOREIGN PATENT DOCUMENTS

| | | | | |
|---|---|---|---|---|
| CN | 101343213 | A * | 1/2009 | B01J 31/24 |
| WO | WO-2014180791 | A1 * | 11/2014 | C07C 29/50 |

OTHER PUBLICATIONS

Zanarotti ("Synthesis and Reactivity of Vinyl Quinone Methides", J. Org. Chem., vol. 50, No. 7, Apr. 1985, pp. 941-945).*
Tanaka et al. ("Assessment of Capsiconinoid Composition, Nonpungent Capsaicinoid Analogues, in Capsicum Cultivars", J. Agric. Food Chem., vol. 57, No. 12, Jun. 2009, pp. 5407-5412).*
U.S. Appl. No. 15/631,647, filed Jun. 23, 2017.*
Zanarotti ("Synthesis and Reactivity of Vinyl Quinone Methides", J. Org. Chem., 1985, 50, pp. 941-945).*
Kanematsu et al. (Synthesis of dehydrodeoxypodophyllotoxin cyclic ether via allene intramolecular cycloaddition strategy and evaluation of its cytotoxicity, Heterocycles, 1991, vol. 32(5), pp. 859-862).*
Berthiol et al. ("Heck Reaction of Protected Allyl Alcohols with Aryl Bromides Catalyzed by a TetraphosphanepalladiumComplex", Eur. J.Org. Chem., 2005, pp. 1367-1377).*
Rio et al. ("Occurrence of Naturally Acetylated Lignin Units", Journal of Agricultural and Food Chemistry, 2007, vol. 55, pp. 5461-5468).*
Fiorentino et al. ("Isolation and Structure Elucidation of Antioxidant Polyphenols from Quince (Cydonia vulgaris) Peels", J. Agric. Food Chem., 2008, vol. 56, pp. 2660-2667).*
Gudla et al. ("Synthesis of Arylnaphthalene Lignan Scaffold by Gold-Catalyzed Intramolecular Sequential Electrophilic Addition and Benzannulation", The Journal of Organic Chemistry, Oct. 2011, vol. 76, pp. 9919-9933).*
Jeong et al. ("Anti-inflammatory phenolics isolated from Juniperus rigida leaves and twigs in lipopolysaccharide-stimulated RAW264.7 macrophage cells", Journal of Enzyme inhibition and Medicinal Chemistry, 2012, vol. 27(6), pp. 875-879).*
Lin et al. ("Visible light photocatalysis of intramolecular radical cation Diels-Alder cycloadditions", Tetrahedron Letters, vol. 53, 2012, pp. 3073-3076).*
Wang et al. ("New Safrole Oxide Derivatives: Synthesis and in vitro Antiproliferative Activities on A549 Human Lung Cancer Cells", Bull. Korean Chem. Soc., 2012, Vo. 33, No. 11, pp. 3571-3575).*
Ambrogio et al., "Unusual Selectivity-Determining Factors in the Phosphine-Free Heck Arylation of Allyl Ethers," Organometallics, 27:3187-3195 (2008).

* cited by examiner

*Primary Examiner* — Joseph R Kosack

(57) ABSTRACT

Precursor or pro-fragrance compounds used as a precursor to deliver at least one fragrant compound that is capable of imparting an odor, in particular one which imparts an odor to a material, more particularly to a fabric or textile. The pro-fragrant compounds of the invention include fragrant alcohols ($R^1OH$) released from a compound of Formula I (I)

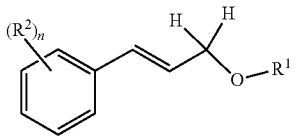

or in which Formula I is derived from ($R^1OH$) and encompass any fragrant alcohol having more than three carbon atoms. Also, methods of generating the fragrant compounds and to improve, enhance or modify odoriferous properties of a perfuming composition or a perfumed article are also disclosed, as are the resultant perfuming compositions and articles.

30 Claims, No Drawings

PRO-FRAGRANCE COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application *is a reissue application of U.S. Pat. No. 10,767,136 B2, which was filed as U.S. patent application Ser. No. 15/351,175 on Nov. 14, 2016, and issued on Sep. 8, 2020, which* claims the benefit of U.S. patent application No. 62/255,361 filed on Nov. 13, 2015 which is incorporated by reference herein in its entirety.

FIELD

The present application relates to the field of perfumery. More particularly, it concerns the use of cinnamyl ether compounds as precursors for the release of fragrant alcohols and aldehydes over a prolonged period.

BACKGROUND

The perfumery industry has a particular interest in compounds which are capable of being released over a prolonged time and that can deliver an odoriferous effect. Various means to control the release of fragrant compounds from pro-fragrances or precursor compounds have been reported. For example compounds have been reported that deliver a fragrance after they are hydrolyzed or exposed to light. In many applications it is desirable to begin and control the release of a fragrance at a time when an article or material containing the precursor is exposed to for example ambient oxygen. Hence, oxidizable pro-fragrances are desirable that can deliver a fragrance over a prolonged period of time after exposure to air.

SUMMARY

Provided herein is a compound of Formula (I)

(I)

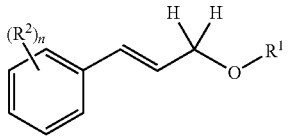

wherein $R^1$ represents a $C_3$ to $C_{20}$ optionally substituted linear, branched or cyclic alkyl; a $C_3$ to $C_{20}$ optionally substituted linear, branched or cyclic, alkenyl; or a $C_3$ to $C_{20}$ optionally substituted linear, branched or cyclic alkynyl group, wherein:

a) each $R^2$ is, independently from each other at each position, hydrogen, hydroxyl group, an optionally substituted $C_1$-$C_6$ alkyl group, a $C_1$-$C_6$ alkoxy group, —O(C═O)$CH_3$ or —O(C═O)CH$(CH_3)_2$;

b) wherein $R^2$ may form an optionally substituted 5 or 6 membered ring;

c) wherein n=5 provided $R^2$ is not hydrogen at every position; and d) provided that Formula I is not 1-(3-isopropoxyprop-1-en-1-yl)-4-methylbenzene, 1-(3-isopropoxyprop-1-en-1-yl)-4-methoxybenzene, 1-butyl-4-(3-isopropoxyprop-1-en-1-yl)benzene, 1-(3-butoxyprop-1-en-1-yl)-4-methylbenzene, 1-(3-butoxyprop-1-en-1-yl)-3-methylbenzene, 2-(3-butoxyprop-1-en-1-yl)-1,3,5-trimethylbenzene, 1-(3-butoxyprop-1-en-1-yl)-4-(tert-butyl)benzene, 1-(3-butoxyprop-1-en-1-yl)-4-methoxybenzene, 1-(3-(tert-butoxy)prop-1-en-1-yl)-4-methylbenzene, 1-(3-(tert-butoxy)prop-1-en-1-yl)-4-methoxybenzene, 1-(3-(tert-butoxy)prop-1-en-1-yl)-4-butylbenzene, (E)-1-(3-((3,7-dimethyloct-6-en-1-yl)oxy)prop-1-en-1-yl)-4-methoxybenzene, 4-(3-((3,7-dimethyloct-6-en-1-yl)oxy)prop-1-en-1-yl)-1,2-dimethoxybenzene, 5-(3-propoxyprop-1-en-1-yl)benzo[d][1,3]dioxole, 5-(3-butoxyprop-1-en-1-yl)benzo[d][1,3]dioxole, 5-(3-pentoxyprop-1-en-1-yl)benzo[d][1,3]dioxole, 5-(3-hexyloxyprop-1-en-1-yl)benzo[d][1,3]dioxole, 1-(3-(benzyloxy)prop-1-en-1-yl)-4-methylbenzene, 1-(3-(benzyloxy)prop-1-en-1-yl)-4-methoxybenzene, 2-(3-(benzyloxy)prop-1-en-1-yl)-1,3,5-trimethylbenzene, 1-(3-(benzyloxy)prop-1-en-1-yl)-4-(tert-butyl)benzene, 4-(3-(benzyloxy)prop-1-en-1-yl)-2-methoxyphenol, 4-(3-(benzyloxy)prop-1-en-1-yl)-2-methoxyphenol, 4-(3-(benzyloxy)prop-1-en-1-yl)-2,6-dimethoxyphenol, 2-methoxy-4-(((3-(3,4,5-trimethoxyphenyl)allyl)oxy)methyl)phenol, (E)-5-(3-(benzyloxy)prop-1-en-1-yl)benzo[d][1,3]dioxole, 5-(((3-(benzo[d][1,3]dioxol-5-yl)allyl)oxy)methyl)benzo[d][1,3]dioxole, 1-(3-(cinnamyloxy)prop-1-en-1-yl)-4-methoxybenzene, 4,4'-(oxybis(prop-1-ene-3,1-diyl))bis(methoxybenzene), 4-(3-(cinnamyloxy)prop-1-en-1-yl)-2-methoxyphenol, or 5-(3-(cinnamyloxy)prop-1-en-1-yl)-1,2,3-trimethoxybenzene.

Further provided is a method of releasing a fragrant compound from a precursor compound, wherein the fragrant compound is selected from the group consisting of a compound of Formula III (III)

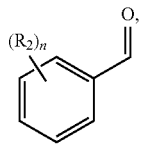

by exposing a precursor compound of Formula I:

(I)

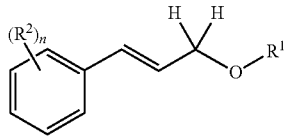

to an environment wherein the compound is oxidized and wherein $R^1$ represents a $C_3$ to $C_{20}$ optionally substituted linear, branched or cyclic alkyl; a $C_3$ to $C_{20}$ optionally substituted linear, branched or cyclic, alkenyl; or a $C_3$ to $C_{20}$ optionally substituted linear, branched or cyclic alkynyl group, wherein $R^2$ is, independently at each position, a hydroxyl group, an optionally substituted $C_1$-$C_6$ alkyl group, a $C_1$-$C_6$ alkoxy group, —O(C═O)$CH_3$ or —O(C═O)CH $(CH_3)_2$ wherein n=5 and any two of $R^2$ may form an optionally substituted 5 or 6 membered ring.

Still yet further provided is a method as recited above wherein the method comprises the release of at least two compounds from the precursor compound wherein at least one of the compounds is a fragrant compound wherein the two compounds are the same or different and each independently comprises the formula (III):

(III)

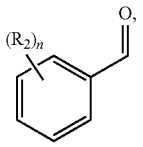

by exposing a precursor compound of Formula I:

(I)

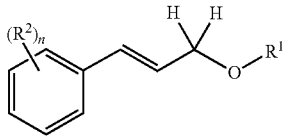

to an environment wherein the compound is oxidized.

And also, the invention relates to the use of a compound of formula (I)

(I)

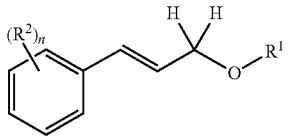

for releasing a fragrant compound from a precursor compound to an environment wherein the compound is oxidized and wherein $R^1$ represents a $C_3$ to $C_{20}$ optionally substituted linear, branched or cyclic alkyl; a $C_3$ to $C_{20}$ optionally substituted linear, branched or cyclic, alkenyl; or a $C_3$ to $C_{20}$ optionally substituted linear, branched or cyclic alkynyl group, wherein $R^2$ is, independently at each position, a hydroxyl group, an optionally substituted $C_1$-$C_6$ alkyl group, a $C_1$-$C_6$ alkoxy group, —O(C═O)$CH_3$ or —O(C═O)CH $(CH_3)_2$ wherein n=5 and any two of $R^2$ may form an optionally substituted 5 or 6 membered ring.

DETAILED DESCRIPTION

For the Summary, Description and Claims, the use of "or" means "and/or" unless stated otherwise. It is to be further understood that where descriptions of various embodiments use the term "comprising," those skilled in the art would understand that in some specific instances, an embodiment can be alternatively described using language "consisting essentially of" or "consisting of."

It is understood that by " . . . hydrocarbon group . . . " it is meant that said group is consisting of hydrogen and carbon atoms and can be in the form of a linear, branched or cyclic, aromatic, alkyl, alkenyl, or alkynyl group, e.g., a linear alkyl group, or can also be in the form of a mixture of said type of groups, e.g. a specific group may comprise a linear alkyl, a branched alkenyl (e.g. having one or more carbon-carbon double bonds), a (poly)cyclic alkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is meant also a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

The term "substantially" as used herein means that most or nearly all. Similarly, "not substantially" is used to me little or none. For example, "not substantially discolored" means that the amount of discoloration, if any, is visibly imperceptible or is at such a low level that it does not connote a defect in product quality. Similarly, "substantially retaining its color" means that the color appearance of the product is essentially the same as the original product or that the change in appearance is not visibly perceptible as providing a defect or detrimental quality aspect to the product.

It is understood that by " . . . alkyl group . . . " it is meant that said group is in the form of a linear, branched or cyclic alkyl group.

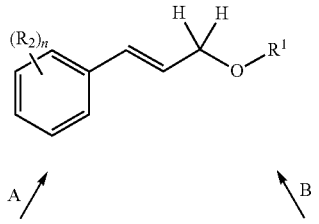

When referring to optionally substituted is meant to comprise $C_1$ to $C_3$ alkoxy, hydroxyl, acyl, optionally substituted aryl (optionally substituted herein means $C_1$ to $C_3$ alkyl, $C_1$ to $C_3$ alkoxy, methylenedioxy, hydroxyl, and acetoxy).

The precursor (pro-fragrance) compounds provided herein are in particular used as a precursor to deliver at least one fragrant compound. A fragrant compound provided herein means a compound which is capable of imparting an odor, in particular one which imparts an odor to a material, more particularly to a fabric or textile. The fragrant alcohols ($R^1OH$) released from a compound of Formula I or which Formula I is derived from ($R^1OH$) are meant to encompass any fragrant alcohol having more than three carbon atoms. While not providing an exhaustive list, provided here is a list of alcohols which are capable of imparting pleasant odors, particularly from surfaces, materials or even air. The fragrant alcohols may be selected from the group consisting such as, but not limited to: anisic alcohol, cinnamic alcohol, fenchylic alcohol, 9-decen-1-ol, phenethylol, citronellol 3-methyl-5-phenyl-1-pentanol (origin: Firmenich SA. Geneva. Switzerland), Mayol® ((4-isopropylcyclohexyl) methanol; origin: Firmenich SA. Geneva. Switzerland), 4-phenylbutan-2-ol, dihydromyrcenol (2,6-dimethyl-7-octen-2-ol), geraniol (3,7-dimethyl-2,6-octadien-1-ol), (Z)-

3-hexen-1-ol, 1-hexanol, 2-hexanol, 5-ethyl-2-nonanol, 2,6-nonadien-1-ol, borneol, 1-octen-3-ol, 4-cyclohexyl-2-methyl-2-butanol (origin: Firmenich SA. Geneva. Switzerland), 2-methyl-4-phenyl-2-butanol, 2-methyl-1-phenyl-2-propanol, cyclomethylcitronellol, decanol, 8-p-menthanol, 3,7-dimethyl-1-octanol, 2,6-dimethyl-2-heptanol, dodecanol, Florol® (tetrahydro-2-isobutyl-4-methyl-4(2H)-pyranol; origin: Firmenich SA. Geneva. Switzerland), linalool, Tarragol® (2-methoxy-4-propyl-1-cylohexanol; origin: Firmenich SA. Geneva, Switzerland), α-terpineol, tetrahydromuguol, 3,7-dimethyl-3-octanol, Lyral® (4-(4-hydroxy-4-methylpentyl)-cyclohex-3-ene-1-carbaldehyde: origin International Flavors and Fragrances. USA), 5,6-dimethyl-1-methylethenylbicyclo[2.2.1]hept-5-ene-2-methanol (Arbozol), 2-phenyethanol, 1-phenylpropanol, 2-phenylpropanol, Lilyflore® ((2,5-dimethyl-2,3-dihydro-1H-inden-2-yl)methanol; origin: Firmenich SA. Geneva. Switzerland), 2,2-dimethyl-3-(3-methylphenyl)-propan-1-ol (Majantol), 2-pentylcyclopentanol, 7-hydroxy-3,7-dimethyloctanal (hydroxycitronellol), 1,1-dimethyl-2-phenylethanol, 4-cyclohexyl-2-methylbutan-2-ol, menthol, 2,6-dimethylheptan-2-ol, 2-tert-butylcyclohexanol, 4-tert-butylcyclohexanol, 2,6-dimethyl-3,5-octadien-2-ol (muguol), 2-methyl-6-methylene-7-octen-2-ol (myrcenol), 3,7,9-trimethyl-1,6-decadien-3-ol (isobutyl linalool), 3,6-dimethyloctan-3-ol, 1,2-dimethyl-3-prop-1-en-2-ylcyclopentan-1-ol (plinol), 2-methyl-4-phenylpentanol (Pamplefleur), 3-methyl-5-phenylpentanol, 3-methyl-5-(2,2,3-trimethyl-1-cyclopent-3-enyl)pentan-2-ol (Sandalore®), (E)-3,3-dimethyl-5-(2,2,3-trimethyl-3-cyclopenten-1-yl)-4-penten-2-ol (Polysantol®), 1-(2,2,6-trimethylcyclohexyl)hexan-3-ol (Norlimbanol™), (E)-4-methyldec-3-en-5-ol, and 4-(4-hydroxyphenyl)butan-2-one.

Many of these ingredients are in any case listed in reference texts such as the book by S. Arctander, Perfume and Flavor Chemicals, 1969, Montclair, N.J., USA, or its more recent versions, or in other works of a similar nature.

In one embodiment provided herein is a compound selected from the group consisting of: (E)-1,2-dimethoxy-4-(3-((2-(4-methylcyclohexyl)propan-2-yl)oxy)prop-1-en-1-yl)benzene compound with (E)-1,2-dimethoxy-4-(3-((2-methyl-4-phenylbutan-2-yl)oxy)prop-1-en-1-yl)benzene and (E)-1,2-dimethoxy-4-(3-(tert-pentyloxy)prop-1-en-1-yl)benzene and (E)-4-((3-(3,4-dimethoxyphenyl)allyl)oxy)-2-isobutyl-4-methyltetrahydro-2H-pyran and (E)-4-(3-((2,6-dimethylheptan-2-yl)oxy)prop-1-en-1-yl)-1,2-dimethoxybenzene (E)-4-(3-((2,6-dimethyloctan-2-yl)oxy)prop-1-en-1-yl)-1,2-dimethoxybenzene and (E)-4-(3-((3,7-dimethylnon-1-en-3-yl)oxy)prop-1-en-1-yl)-1,2-dimethoxybenzene and (E)-4-(3-((4-cyclohexyl-2-methylbutan-2-yl)oxy)prop-1-en-1-yl)-1,2-dimethoxybenzene (E)-4-(3-(tert-butoxy)prop-1-en-1-yl)-1,2-dimethoxybenzene and 4-((E)-3-(((E)-3,7-dimethylnona-1,6-dien-3-yl)oxy)prop-1-en-1-yl)-1,2-dimethoxybenzene, (E)-S-(3-((2,6-dimethylheptan-2-yl)oxy)prop-1-en-1-yl)benzo[d][1,3]dioxole compound with (E)-5-(3-((2,6-dimethyloctan-2-yl)oxy)prop-1-en-1-yl)benzo[d][1,3]dioxole and (E)-5-(3-((2-(4-methylcyclohexyl)propan-2-yl)oxy)prop-1-en-1-yl)benzo[d][1,3]dioxole and (E)-5-(3-((2-isobutyl-4-methyltetrahydro-2H-pyran-4-yl)oxy)prop-1-en-1-yl)benzo[d][1,3]dioxole and (E)-5-(3-((2-methyl-4-phenylbutan-2-yl)oxy)prop-1-en-1-yl)benzo[d][1,3]dioxole and (E)-5-(3-((3,7-dimethylnon-1-en-3-yl)oxy)prop-1-en-1-yl)benzo[d][1,3]dioxole and (E)-5-(3-((3,7-dimethylnonan-3-yl)oxy)prop-1-en-1-yl)benzo[d][1,3]dioxole and (E)-5-(3-((4-cyclohexyl-2-methylbutan-2-yl)oxy)prop-1-en-1-yl)benzo[d][1,3]dioxole and (E)-5-(3-(tert-butoxy)prop-1-en-1-yl)benzo[d][1,3]dioxole and (E)-5-(3-(tert-pentyloxy)prop-1-en-1-yl)benzo[d][1,3]dioxole and 5-((E)-3-(((E)-3,7-dimethylnona-1,6-dien-3-yl)oxy)prop-1-en-1-yl)benzo[d][1,3]dioxole, (E)-1-(3-((2,6-dimethylheptan-2-yl)oxy)prop-1-en-1-yl)-4-ethylbenzene compound with (E)-1-(3-((2,6-dimethyloctan-2-yl)oxy)prop-1-en-1-yl)-4-ethylbenzene and (E)-1-(3-((3,7-dimethylnon-1-en-3-yl)oxy)prop-1-en-1-yl)-4-ethylbenzene and (E)-1-(3-((3,7-dimethylnonan-3-yl)oxy)prop-1-en-1-yl)-4-ethylbenzene and (E)-1-(3-((4-cyclohexyl-2-methylbutan-2-yl)oxy)prop-1-en-1-yl)-4-ethylbenzene and (E)-1-(3-(tert-butoxy)prop-1-en-1-yl)-4-ethylbenzene and (E)-1-ethyl-4-(3-((2-(4-methylcyclohexyl)propan-2-yl)oxy)prop-1-en-1-yl)benzene and (E)-1-ethyl-4-(3-((2-methyl-4-phenylbutan-2-yl)oxy)prop-1-en-1-yl)benzene and (E)-1-ethyl-4-(3-(tert-pentyloxy)prop-1-en-1-yl)benzene and (E)-4-((3-(4-ethylphenyl)allyl)oxy)-2-isobutyl-4-methyltetrahydro-2H-pyran and 1-((E)-3-(((E)-3,7-dimethylnona-1,6-dien-3-yl)oxy)prop-1-en-1-yl)-4-ethylbenzene, (E)-1,2-dimethoxy-4-(((3-(4-methoxyphenyl)allyl)oxy)methyl)benzene compound with (E)-4-(3-((3,4-dimethoxybenzyl)oxy)prop-1-en-1-yl)-1,2-dimethoxybenzene and (E)-5-(((3-(3,4-dimethoxyphenyl)allyl)oxy)methyl)benzo[d][1,3]dioxole and (E)-5-(((3-(4-methoxyphenyl)allyl)oxy)methyl)benzo[d][1,3]dioxole and (E)-5-(3-((3,4-dimethoxybenzyl)oxy)prop-1-en-1-yl)benzo[d][1,3]dioxole and 1,2-dimethoxy-4-((E)-3-(((E)-3-(4-methoxyphenyl)allyl)oxy)prop-1-en-1-yl)benzene and 4,4'-((1E,1'E)-oxybis(prop-1-ene-3,1-diyl))bis(1,2-dimethoxybenzene) and 5-((E)-3-(((E)-3-(3,4-dimethoxyphenyl)allyl)oxy)prop-1-en-1-yl)benzo[d][1,3]dioxole and 5-((E)-3-(((E)-3-(4-methoxyphenyl)allyl)oxy)prop-1-en-1-yl)benzo[d][1,3]dioxole, In another embodiment provided herein is a compound selected from the group consisting of A compound selected from the group consisting of (E)-2-methoxy-4-(3-propoxyprop-1-en-1-yl)phenol, (E)-4-(3-butoxyprop-1-en-1-yl)-2-methoxyphenol, (E)-2-methoxy-4-(3-(pentyloxy)prop-1-en-1-yl)phenol, (E)-4-(3-(hexyloxy)prop-1-en-1-yl)-2-methoxyphenol, (E)-2-methoxy-4-(3-(octyloxy)prop-1-en-1-yl)phenol, (E)-2-methoxy-4-(3-(nonyloxy)prop-1-en-1-yl)phenol, (E)-4-(3-(decyloxy)prop-1-en-1-yl)-2-methoxyphenol, (E)-2-methoxy-4-(3-(undecyloxy)prop-1-en-1-yl)phenol, (E)-4-(3-(dodecyloxy)prop-1-en-1-yl)-2-methoxyphenol, (E)-2-methoxy-4-(3-(octadecyloxy)prop-1-en-1-yl)phenol, 4-((E)-3-(((1s,4s)-4-isopropylcyclohexyl)methoxy)prop-1-en-1-yl)-2-methoxyphenol, (E)-4-(3-((3,7-dimethyloctyl)oxy)prop-1-en-1-yl)-2-methoxyphenol, 4-((E)-3-(((E)-3,7-dimethylocta-2,6-dien-1-yl)oxy)prop-1-en-1-yl)-2-methoxyphenol, (E)-4-(3-((3,7-dimethyloct-6-en-1-yl)oxy)prop-1-en-1-yl)-2-methoxyphenol, (E)-4-(3-((4-isopropylbenzyl)oxy)prop-1-en-1-yl)-2-methoxyphenol, (E)-4-(3-(dec-9-en-1-yloxy)prop-1-en-1-yl)-2-methoxyphenol, 2-methoxy-44(E)-3-(((Z)-non-6-en-1-yl)oxy)prop-1-en-1-yl)phenol, 4-((E)-3-(((E)-hex-2-en-1-yl)oxy)prop-1-en-1-yl)-2-methoxyphenol, 4-((E)-3-(((Z)-hex-3-en-1-yl)oxy)prop-1-en-1-yl)-2-methoxyphenol, 2-methoxy-4-((E)-3-(((2E,6E)-nona-2,6-dien-1-yl)oxy)prop-1-en-1-yl)phenol, (E)-2-methoxy-4-(3-((3-methyl-5-phenylpentyl)oxy)prop-1-en-1-yl)phenol, (E)-2-methoxy-4-(3-(2-phenylpropoxy)prop-1-en-1-yl)phenol, (E)-2-methoxy-4-(3-(3-phenylpropoxy)prop-1-en-1-yl)phenol, (E)-2-methoxy-4-(3-phenethoxyprop-1-en-1-yl)phenol, (E)-4-(3-((2,5-dimethyl-2,3-dihydro-1H-inden-2-yl)methoxy)prop-1-en-1-yl)-2-methoxyphenol, (R,E)-2-methoxy-4-(3-((4-(prop-1-en-2-yl)cyclohex-1-en-1-yl)methoxy)prop-1-en-1-yl)phenol, 4-((E)-3-(cinnamyloxy)prop-1-en-1-yl)-2-methoxyphenol, (E)-4-(3-((4-hydroxy-3-methoxybenzyl)oxy)prop-1-en-1-yl)-2-methoxyphenol, (E)-2-methoxy-4-(3-((4-methoxybenzyl)oxy)prop-1-en-1-yl)phenol, (E)-4-(3-((3,4-dimethoxybenzyl)oxy)prop-1-en-1-yl)-2-methoxyphenol, (E)-4-(3-(benzo[d][1,3]dioxol-5-ylmethoxy)prop-1-en-1-yl)-2-methoxyphenol, (E)-2-methoxy-4-(3-(1-phenylethoxy)prop-1-en-1-yl)phenol, (E)-2-methoxy-4-(3-(undecan-2-yloxy)prop-1-en-1-yl)phenol, (E)-2-methoxy-4-(3-(2-pentylcyclopentyl)oxy)prop-1-en-1-yl)phenol, (E)-4-(3-((5-isopropyl-2-methylcyclohexyl)oxy)prop-1-en-1-yl)-2-methoxyphenol, 2-methoxy-4-((E)-3-(((E)-4-methyldec-3-en-5-yl)oxy)prop-1-en-1-yl)phenol, (R,E)-4-(3-((1-isopropyl-4-methylcyclohex-3-en-1-yl)oxy)prop-1-en-1-yl)-2-methoxyphenol, (E)-4-(3-(cyclohexyloxy)prop-1-en-1-yl)-2-methoxyphenol, (E)-4-(3-(heptan-3-yloxy)prop-1-en-1-yl)-2-methoxyphenol, 2-methoxy-4-((E)-3-(((1S,2R,4S)-1,7,7-trimethylbicyclo[2.2.1]heptan-2-yl)oxy)prop-1-en-1-yl)phenol, (E)-2-methoxy-4-(3-(oct-1-en-3-yloxy)prop-1-en-1-yl)phenol, 2-methoxy-4-((E)-3-(((1R,2R,4S)-1,3,3-trimethylbicyclo[2.2.1]heptan-2-yl)oxy)prop-1-en-1-yl)phenol, (E)-2-ethyl-3-((3-(4-hydroxy-3-methoxyphenyl)allyl)oxy)-4H-pyran-4-one, (E)-2-methoxy-4-(3-((7-methoxy-3,7-dimethyloctan-2-yl)oxy)prop-1-en-1-yl)phenol, (E)-2-methoxy-4-(3-((2-methoxy-4-propylcyclohexyl)oxy)prop-1-en-1-yl)phenol, (E)-3-((3-(4-hydroxy-3-methoxyphenyl)allyl)oxy)butan-2-one, (E)-4-((3-(4-hydroxy-3-methoxyphenyl)allyl)oxy)-2,5-dimethylfuran-3(2H)-one, (E)-3-((3-(4-hydroxy-3-methoxyphenyl)allyl)oxy)-2-methyl-4H-pyran-4-one, (E)-4-(3-(tert-butoxy)prop-1-en-1-yl)-2-methoxyphenol, (E)-2-methoxy-4-(3-(tert-pentyloxy)prop-1-en-1-yl)phenol, (E)-4-(3-((2-isobutyl-4-methyltetrahydro-2H-pyran-4-yl)oxy)prop-1-en-1-yl)-2-methoxyphenol, (E)-2-methoxy-4-(3-((2-methyl-4-phenylbutan-2-yl)oxy)prop-1-en-1-yl)phenol, 4-((E)-3-(((E)-3,7-dimethylnona-1,6-dien-3-yl)oxy)prop-1-en-1-yl)-2-methoxyphenol, (E)-4-(3-((3,7-dimethylnon-1-en-3-yl)oxy)prop-1-en-1-yl)-2-methoxyphenol, (E)-4-(3-((3,7-dimethylnonan-3-yl)oxy)prop-1-en-1-yl)-2-methoxyphenol, (E)-4-(3-((2,6-dimethyloct-7-en-2-yl)oxy)prop-1-en-1-yl)-2-methoxyphenol, (E)-4-(3-((2,6-dimethyloctan-2-yl)oxy)prop-1-en-1-yl)-2-methoxyphenol, (E)-4-(3-((4-cyclohexyl-2-methylbutan-2-yl)oxy)prop-1-en-1-yl)-2-methoxyphenol, (E)-4-(3-((2,6-dimethylheptan-2-yl)oxy)prop-1-en-1-yl)-2-methoxyphenol, (E)-2-methoxy-4-(3-((2-(4-methylcyclohexyl)propan-2-yl)oxy)prop-1-en-1-yl)phenol, (E)-4-(3-((3,7-dimethyloct-1-en-3-yl)oxy)prop-1-en-1-yl)-2-methoxyphenol, (E)-4-(3-((3,7-dimethyloctan-3-yl)oxy)prop-1-en-1-yl)-2-methoxyphenol, (E)-4-(3-((3,7-dimethylocta-1,6-dien-3-yl)oxy)prop-1-en-1-yl)-2-methoxyphenol, 4,4'-((1E,1'E)-oxybis(prop-1-ene-3,1-diyl))bis(2-methoxyphenol), 2-methoxy-4-((E)-3-(((E)-3-(4-methoxyphenyl)allyl)oxy)prop-1-en-1-yl)phenol, 4-((E)-3-(((E)-3-(3,4-dimethoxyphenyl)allyl)oxy)prop-1-en-1-yl)-2-methoxyphenol, 4-((E)-3-(((E)-3-(4-ethoxyphenyl)allyl)oxy)prop-1-en-1-yl)-2-methoxyphenol, 4-((E)-3-(((E)-3-(benzo[d][1,3]dioxol-5-yl)allyl)oxy)prop-1-en-1-yl)-2-methoxyphenol, 1,2-dimethoxy-4-((E)-3-(((E)-3-(4-methoxyphenyl)allyl)oxy)prop-1-en-1-yl)benzene, 5,5'-((1E,1'E)-oxybis(prop-1-ene-3,1-diyl))bis(benzo[d][1,3]dioxole), 4-((E)-3-(((E)-3-(4-ethylphenyl)allyl)oxy)prop-1-en-1-yl)-2-methoxyphenol.

In another embodiment provided herein is a compound selected from the group consisting of:

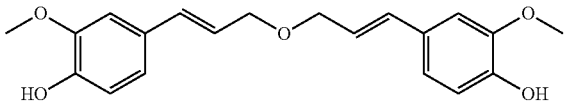

4,4'-((1E,1'E)-oxybis(prop-1-ene-3,1-diyl))bis(2-methoxyphenol)

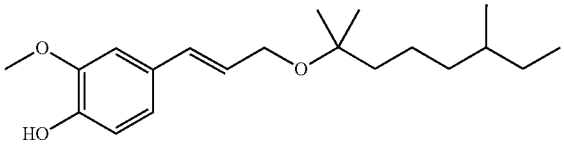

(E)-4-(3-((2,6-dimethyloctan-2-yl)oxy)prop-1-en-1-yl)-2-methoxyphenol

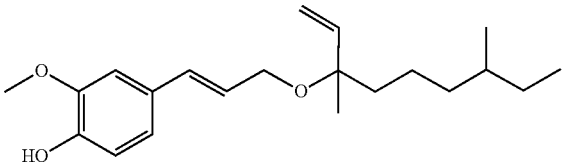

(E)-4-(3-((3,7-dimethylnon-1-en-3-yl)oxy)prop-1-en-1-yl)-2-methoxyphenol

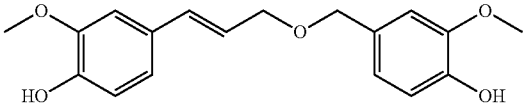

(E)-4-(3-((4-hydroxy-3-methoxybenzyl)oxy)prop-1-en-1-yl)-2-methoxyphenol

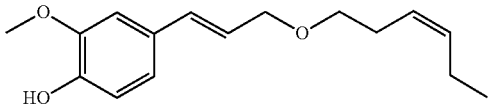

4-((E)-3-(((Z)-hex-3-en-1-yl)oxy)prop-1-en-1-yl)-2-methoxyphenol

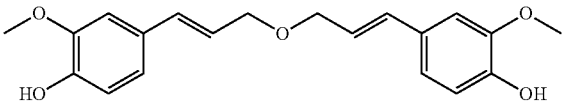

2-ethoxy-4-((E)-3-(((E)-3-(4-hyroxy-3-methoxyphenyl)allyl)oxy)prop-1-en-1-yl)phenol

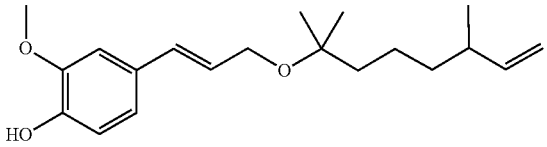

(E)-4-(3-((2,6-dimethyloct-7en-2-yl)oxy)prop-1-en-1-yl)-2-methoxyphenol

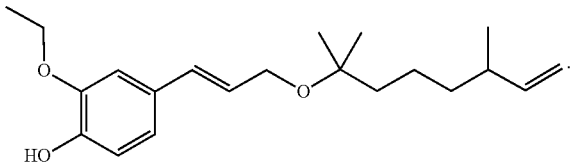

(E)-4-(3-((2,6-dimethyloct-7-en-2yl)oxy)prop-1-en-1-yl)-2-ethoxyphenol

In another aspect is a method to improve, enhance or modify the odoriferous properties of a perfuming composition or a perfumed article, which method comprises adding to said composition or article an effective amount of a compound of Formula I.

In yet another embodiment, provided herein is a perfumed article comprising a compound provided herein wherein the perfumed article is provided in a perfumed product selected from the group consisting of perfume, cologne, bath gel, shower gel, hair-care product, cosmetic preparation, body deodorant, solid or liquid air-freshener, detergent, fabric softener, and all purpose cleaner.

In another embodiment provided herein is a method as described wherein a compound provided herein is exposed to the environment through a perfumed article comprising the compound wherein the perfumed article is provided in a perfumed product selected from the group consisting of a perfume, a cologne, a bath gel, a shower gel, a hair-care product, a cosmetic preparation, a soap bar, a body wash, a body deodorant, a solid or liquid air-freshener, a fabric refreshener, a candle, a laundry detergent, a fabric softener, a lotion, softener or wash in form of a powder, a liquid or a tablet, a shampoo, a hair conditioner, a leave-in hair conditioner, or a hairspray.

In a particular embodiment the perfumed product is an all-purpose household cleaner, a window cleaner, and a furniture polish.

A compound of Formula I provided herein may be used for the controlled release of perfuming ingredients from a surface treated with a product identified above. This use, for example concerns a method to confer, enhance, improve or modify the odor properties of a perfuming composition, of an article or of a surface. A "surface" may include but not be limited to skin, hair, a hard surfaces (e.g., but not limited to kitchen counter-tops, glass, hardwood floors, tile, bath tub and sink surfaces and fixtures), fabrics (e.g., but not limited to carpet, clothes, upholstery, curtains, car interiors). In a particular embodiment, the pro-fragrance is applied to a material such as a fabric or textile upon the process of washing material or treating it with a fabric softener. In one aspect, the perfuming effect of such compounds can be to prolong and/or intensify a perfuming effect upon the exposure of the material on a surface to ambient air.

In one embodiment, the released compound from a compound of Formula I is vanillin. In a particular embodiment, a product having vanillin as the released compound of Formula I is not substantially discolored. Vanillin is a very desirable aromatic compound that can used in perfumes and perfumed products. However it has long been known that it discolors products. For example, when vanillin is added as a fragrant compound to a white bar soap it will quickly turn the soap yellow and then further turn it brown. Similarly it is known to discolor clear or white detergents. We have found that it also discolors lotions, fabric refreshers and hair conditioners. Compounds of Formula I that will release vanillin do not substantially discolor products that would otherwise be discolored as the result of the addition of vanillin. Further, when a product, as described above, is used to treat a surface the compound of Formula I will become effectively deposited on the surface such that the compound will be released (e.g., but not limited to vanillin) when exposed to ambient conditions it will release a desirable vanillin note. Hence, this overcomes a long felt need to provide the use of vanillin in a perfumed product without a problem of discoloration or deposition with the release of a very describable vanillin aroma.

A desirable aroma vanillin odor known to discolor darkens for example an otherwise clear solution, when the vanillin is added to the solution. Is has been particularly difficult to formulate a perfume containing vanillin that substantially retains its original color or clarity.

In another aspect, the controlled release of a perfuming compound provided herein comprises adding to a composition or an article an effective amount of a compound (I) which is capable of imparting an odor to fabrics, textiles, skin, hard surfaces, hair when oxidized after the process of washing with a detergent or with the treatment of a fabric softener. The release of the fragrance provided herein is sustained particularly for a period of greater than 1 day, most particularly greater than 1 week, and even more particularly greater than 2 weeks. In many applications it is desirable to begin and control the release of a fragrance at a time when an article or material, containing the precursor or which the precursor has been deposited on, is exposed to for example ambient oxygen.

In another embodiment, provided herein is a fragrance delivery system comprising a compound of Formula I which provides a long-lasting odor of volatile fragrance from a product or from a product deposited on a material. The release of the above-mentioned fragrant compounds from the compounds and delivery system described herein occurs upon the exposure for example of a precursor compound according to Formula I to oxygen or other oxidizing agents.

In another embodiment, a compound or method provided herein can be used in functional perfumery. Particularly, the precursor compounds and methods provided herein can be used in applications such as liquid or solid detergents for the treatment of textiles and fabric softeners, in which the fragrance of the ingredients must be effectively imparted to the textile during washing.

In one embodiment provided herein vanillin is released from a compound of Formula I. Particularly the profragrance or a compound of Formula I is vanillin and it is released or deposited from the compound.

In particular applications (perfumed products) described herein, compounds provided herein have a noticeable olfactive performance (for example but not limited to vanilla odor intensity) at or above 0.5%, by weight, of the total weight of the product, more particularly at or above 0.2%, by weight, of the total weight of the product, even more particularly at or above 0.1% by weight, of the total weight of the product. In one embodiment, a compound provided herein has a noticeable olfactive performance in a perfumed product from about 0.1% up to about 0.2%, by weight, of the total weight of the product.

EXAMPLES

The invention will now be described in further detail by way of the following examples. These examples are not intended to be limiting and are for illustrative purposes only.

Example 1

Cinnamyl Ethers by the Heck Reaction

Following a reported procedure (Ambrogio, I.; Fabrizi, G.; Cacchi, S.; Henriksen, S. T.; Fristrup, R.; Tanner, D.; Norrby, P.-O. Organometallics 2008, 27, 3187-3195), cinnamyl ethers are prepared by the Heck reaction between aryl halides and allyl ethers prepared from perfumery alcohols.

In a typical procedure, the perfume alcohol is slowly added to a mixture of NaH (60% in mineral oil) in DMF under a $N_2$ atm. Using an addition funnel, allyl bromide is added at a rate that allows the ensuing exotherm to maintain a temperature of the mixture at about 70° C. The mixture is stirred an additional 15 min and then water is added. The mixture is then diluted with diethyl ether, and after washing with water, the organic phase is dried with $Na_2SO_4$, filtered and concentrated. After silica gel flash chromatography, sometimes followed by bulb-to-bulb distillation, the allyl ethers are obtained as liquids in yields of 29-90%.

The aryl halide is added to a mixture of the allyl ether, tetrabutylammonium acetate, palladium (II) acetate and DMF. The mixture is placed in a preheated 90° C. oil bath. The reaction progress is monitored by GC analysis and upon consumption of the aryl halide (0.5-2 h for aryl iodides and 16-24 h for aryl bromides), the reaction mixture is removed from the oil bath. Water and diethyl ether are added to the mixture and the resulting emulsion is filtered through a pad of Celite® prior to separating the phases. The ether phase is dried ($Na_2SO_4$), filtered and concentrated. Flash chromatography (silica gel) of the crude product (hexane/$CH_2Cl_2$/EtOAc) yields colorless to pale amber oils that are composed predominantly of the desired cinnamyl ethers.

Example 1.1: 4-((E)-3-(((Z)-hex-3-en-1-yl)oxy) prop-1-en-1-yl)-2-methoxyphenol Starting from (Z)-hex-3-en-1-ol (pipol), allyl bromide, NaH and DMF, (Z)-1(allyloxy)hex-3-ene was obtained. Using this allyl ether, 4-bromo-2-methoxyphenol, tetrabutylammonium acetate, $Pd(OAc)_2$ and DMF the title compound was obtained after flash chromatography (hexane/EtOAc).

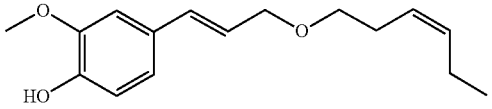

$^1$H NMR ($CDCl_3$, 500 MHz): δ 0.97 (t, J=7.5 Hz, 3H), 2.07 (quintet, J=7.5 Hz, 2H), 2.37 (q, J=7.2 Hz, 2H), 3.47 (t, J=7.2 Hz, 2H), 3.88 (s, 3H), 4.13 (dd, J=6.3, 1.3 Hz, 2H), 5.32-5.40 (m, 1H), 5.44-5.52 (m, 1H), 5.74 (s, 1H), 6.14 (dt, J=15.8, 6.2 Hz, 1H), 6.52 (d, J=15.8 Hz, 1H), 6.83-6.93 (m, 3H).

MS (EI): 262 (13, $M^+$), 179 (12), 178 (11), 163 (22), 150 (21), 149 (25), 137 (32), 132 (13), 131 (100), 118 (29), 102 (52), 91 (35), 76 (15), 64 (10), 55 (31), 41 (32), 39, (14).

Example 1.2: (E)-2-methoxy-4-(3-(undecan-2-yloxy)prop-1-en-1-yl)phenol

Starting from undecan-2-ol (methylnonylcarbinol), allyl bromide, NaH and DMF, 2-(allyloxy)undecane was obtained. Using this allyl ether, 4-bromo-2-methoxyphenol, tetrabutylammonium acetate, $Pd(OAc)_2$ and DMF, the title compound was obtained after flash chromatography (hexane/EtOAc).

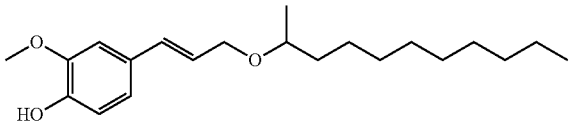

$^1$H NMR ($CDCl_3$, 500 MHz): δ 0.88 (t, J=7.0 Hz, 3H), 1.17 (d, J=6.2 Hz, 3H), 1.20-1.68 (m, 16H), 3.49 (sextet, J=6.0 Hz, 1H), 3.89 (s, 3H), 4.07 (ddd, J=12.3, 6.4, 1.5 Hz, 1H), 4.17 (ddd, J=12.3, 6.4, 1.5 Hz, 1H), 5.65 (s, 1H), 6.14 (dt, J=15.8, 6.2 Hz, 1H), 6.51 (d, J=15.8 Hz, 1H), 6.78-7.0 (m, 3H).

MS (EI): 334 ($M^+$, 15), 180 (35), 179 (100), 163 (19), 151 (43), 131 (48), 119 (32), 103 (28), 91 (24), 43 (22).

Example 1.3: (E)-2-methoxy-4-(3-(tert-pentyloxy) prop-1-en-1yl)phenol

Starting from 2-methylbutan-2-ol, allyl bromide, NaH and DMF, 2-(allyloxy)-2-methylbutane was obtained. Using this allyl ether, 4-bromo-2-methoxyphenol, tetrabutylammonium acetate, $Pd(OAc)_2$ and DMF, the title compound was obtained after flash chromatography (hexane/EtOAc).

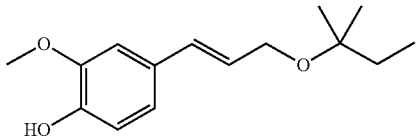

$^1$H NMR ($CDCl_3$, 500 MHz): δ 0.91 (t, 7.5 Hz, 3H), 1.20 (s, 6H), 1.56 (q, J=7.5 Hz, 2H), 3.85 (s, 3H), 4.01 (dd, J=6.1, 1.4 Hz, 2H), 5.74 (s, 1H), 6.12 (dt, J=15.8, 6.0 Hz, 1H), 6.50 (d, J=15.8 Hz, 1H), 6.81-6.93 (m, 3H).

MS (EI): 250 (20, $M^+$), 180 (85), 179 (79), 163 (51), 151 (65), 137 (40), 131 (100), 119 (78), 103 (56), 91 (57), 71 (58), 55 (72), 43 (73).

Example 1.4: (E)-4-(3-((2,6,dimethyloct-7-en-2-yl) oxy)prop-1-en-1-yl)-2-methoxyphenol Starting from 2,6-dimethyloct-7-en-2-ol (dihydromyrcenol), allyl bromide, NaH and DMF, 7-(allyloxy)-3,7-dimethyloct-1-ene was obtained. Using this allyl ether, 4-iodo-2-methoxyphenol, tetrabutylammonium acetate, $Pd(OAc)_2$ and DMF, the title compound was obtained after flash chromatography (hexane/EtOAc).

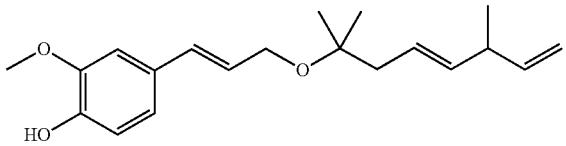

$^1$H NMR ($CDCl_3$, 500 MHz): δ 0.99 (d, 6.7 Hz, 3H), 1.20 (s, 6H), 1.24-1.41 (m, 4H), 1.43-1.54 (m, 2H), 2.13 (m, 1H), 3.87 (s, 3H), 4.01 (d, J=6.0 Hz, 2H), 4.91 (d, J=10.4 Hz, 1H), 4.96 (d, J=17.4 Hz, 1H), 5.69 (ddd, J=17.4, 10.4, 7.5 Hz, 1H), 5.71 (s, 1H), 6.12 (dt, J=15.8, 6.0 Hz, 1H), 6.5 (d, J=15.8 Hz, 1H), 6.80-6.95 (m, 3H).

MS (EI): 318 (12, $M^+$), 180 (100), 179 (85), 163 (56), 151 (41), 131 (88), 119 (39), 103 (43), 83 (47), 55 (60).

Example 2

Example 2.1 Application in Leave-On Hair Conditioner

The general formulation for base MTK 05 012 consisted of 95% water, 1% Salcare SC 91, 1% Aculyn 46, 0.5% Wacker-Belsil DMC 6038, 0.5% Phenonip and 1.5% Mirasil ADM-E. 0.5 wt % (E)-4-(3-((2,6-dimethyloct-7-en-2-yl)oxy)prop-1-en-1-yl)-2-methoxyphenol (Ex. 1.4) was added to the base. This was aged for 24 h prior to use. A second sample containing vanillin and dihydromyrcenol at equimolar levels to the profragrance was prepared as a reference and aged for same time period.

The hair tresses were washed with 5 g unfragranced shampoo for 30 s, rinsed under running tap water for 30 s and repeated. 0.2 g of leave-on conditioner with profragrance or the perfumery raw materials was applied to the tresses. The product was stroked into the hair, combed and hung to dry. Olfactive evaluations by a five-membered panel (including a perfumer) of the tresses were conducted at 2, 6 and 24 h. The samples were rated for vanillin intensity on a scale of 0-7, with 7 being the strongest. The profragrance sample was rated stronger than the reference at all time points (Table 1).

TABLE 1

Olfactive evaluation of Ex. 1.4 on hair tresses

| Time | Control Strength (0-7) | Precursor Strength (0-7) | Perfumer's olfactive descriptors of profragrance |
|---|---|---|---|
| 2 hrs | 3 | 4 | Very clear vanilla |
| 6 hrs | 3 | 6 | note at all time points |
| 24 hrs | 2 | 7 | |

Example 2.2 Application in Leave-On Hair Conditioner

Using a procedure similar to Ex. 2.1 (leave-on hair conditioner, 0.5% dosage) hair tresses were treated with each of the following: Ex. 1.1, 1.2, 1.3 or 1.4. The hair tresses were left to dry for twenty-four hours prior to evaluation. A set of 19 expert panelists were asked to evaluated the tresses for vanillin odor. The number of panelists still detecting vanillin after twenty-four hours and the average intensity rating are listed in Table 2. In all cases, a vanillin odor was detected by a majority of the panelists.

TABLE 2

Olfactive evaluation
Intensity Rating 0-10

| | Ex. 1.1 | Ex. 1.2 | Ex. 1.3 | Ex. 1.4 |
|---|---|---|---|---|
| # of people detecting vanillin release | 16/19 | 17/19 | 19/19 | 19/19 |

Example 7

Color Assessment in Different Applications

Ex. 1.4 was dosed at 0.5 wt % into a skin lotion, a leave on hair conditioner, and a fabric refresher (pH 5). Corresponding control samples were prepared by dosing vanillin and dihydromyrcenol into the various applications at a level equimolar to the profragrance. The samples were stored in clear glass vials at room temperature on a laboratory bench. Periodic inspection showed the vanillin-containing samples developed a much darker color than the samples containing Ex. 1.4 which discolored much less. After 4 months, a spectrophotometric color analysis (Hunter ColorQuest XE in transmittance mode) was performed on the fabric refresher samples. The measured colors—reported here as CIELAB values (D65 light and 10° observer)—are reported in Table 3. The data show that the profragrance-containing sample was significantly lighter in color compared to the control sample.

TABLE 3

Color analysis of Ex. 1.4 in fabric refresher (LAB values)

| | Profragrance | Control |
|---|---|---|
| L | 72.77 | 9.6 |
| A | 16.83 | 18.45 |
| B | 43.71 | 7.87 |

What is claimed is:

1. A compound of Formula (I)

(I)

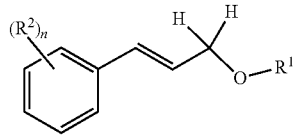

wherein said compound is capable of releasing upon oxidation an alcohol of formula $R^1OH$ selected from the group consisting of anisic alcohol, fenchylic alcohol, 9-decen-1-ol, phenethylol, citronellol, 3-methyl-5-phenyl-1-pentanol, (4-isopropylcyclohexyl)methanol, 4-phenylbutan-2-ol, 2,6-dimethyl-7-octen-2-ol, 3,7-dimethyl-2,6-octadien-1-ol, (Z)-3-hexen-1-ol, 2-hexanol, 5-ethyl-2-nonanol, 2,6-nonadien-1-ol, borneol, 1-octen-3-ol, 4-cyclohexyl-2-methyl-2-butanol, 2-methyl-4-phenyl-2-butanol, 2-methyl-1-phenyl-2-propanol, cyclomethylcitronellol, decanol, 8-p-menthanol, 3,7-dimethyl-1-octanol, 2,6-dimethyl-2-heptanol, dodecanol, tetrahydro-2-isobutyl-4-methyl-4(2H)-pyranol, linalool, 2-methoxy-4-propyl-1-cylohexanol, α-terpineol, tetrahydromuguol, 3,7-dimethyl-3-octanol, 5,6-dimethyl-1-methylethenylbicyclo[2.2.1]hept-5-ene-2-methanol, 2-phenyethanol, 1-phenylpropanol, 2-phenylpropanol, (2,5-dimethyl-2,3-dihydro-1H-inden-2-yl)methanol, 2,2-dimethyl-3-(3-methylphenyl)-propan-1-ol, 2-pentylcyclopentanol, 1,1-dimethyl-2-phenylethanol, 4-cyclohexyl-2-methylbutan-2-ol, menthol, 2,6-dimethylheptan-2-ol, 2-tert-butylcyclohexanol, 4-tert-butylcyclohexanol, 2,6-dimethyl-3,5-octadien-2-ol, 2-methyl-6-methylene-7-octen-2-ol, 3,7,9-trimethyl-1,6-decadien-3-ol, 3,6-dimethyloctan-3-ol, 1,2-dimethyl-3-prop-1-en-2-ylcyclopentan-1-ol, 2-methyl-4-phenylpentanol, 3-methyl-5-phenylpentanol, 3-methyl-5-(2,2,3-trimethyl-1-cyclopent-3-enyl) pentan-2-ol, (E)-3,3-dimethyl-5-(2,2,3-trimethyl-3-cyclopenten-1-yl)-4-penten-2-ol, 1-(2,2,6-trimethylcyclohexyl)hexan-3-ol, (E)-4-methyldec-3-en-5-ol, 4-(4-hydroxyphenyl)butan-2-ol, 4-(3-hydroxyprop-1-en-1-yl)-2-methoxyphenol, 4-(3-hydroxyprop-1-en-1-yl)-2-ethoxyphenol, 2,6-dimethyloctan-2-ol, 3,7-dimethylnon-1-en-3-ol, wherein:

a) the alcohol of formula $R^1OH$ is derived from the

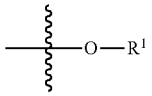

moiety of the compound of Formula (I), such that $R^1$ moiety of the alcohol of formula $R^1OH$ corresponds to the $R^1$ moiety of the compound of Formula (I);

b) each $R^2$ is, independently from each other at each position, hydrogen, hydroxyl group, an optionally substituted $C_1$-$C_6$ alkyl group, a $C_1$-$C_6$ alkoxy group, —O(C═O)$CH_3$ or —O(C═O)$CH(CH_3)_2$;

c) wherein $R^2$ may form an optionally substituted 5 or 6 membered ring;

d) wherein n=5 provided that $R^2$ is not hydrogen at every position; and e) provided that Formula I is not 1-(3-isopropoxyprop-1-en-1-yl)-4-methylbenzene, 1-(3-isopropoxyprop-1-en-1-yl)-4-methoxybenzene, 1-butyl-4-(3-isopropoxyprop-1-en-1-yl)benzene, 1-(3-butoxyprop-1-en-1-yl)-4-methylbenzene, 1-(3-butoxyprop-1-en-1-yl)-3-methylbenzene, 2-(3-butoxyprop-1-en-1-yl)-1,3,5-trimethylbenzene, 1-(3-butoxyprop-1-en-1-yl)-4-(tert-butyl)benzene, 1-(3-butoxyprop-1-en-1-yl)-4-methoxybenzene, 1-(3-(tert-butoxy)prop-1-en-1-yl)-4-methylbenzene, 1-(3-(tertbutoxy) prop-1-en-1-yl)-4-methoxybenzene, 1-(3-(tert-butoxy)prop-1-en-1-yl)-4-butylbenzene, (E)-1-(3-((3,7-dimethyloct-6-en-1-yl) oxy)prop-1-en-1-yl)-4-methoxybenzene, 4-(3-((3,7-dimethyloct-6-en-1-yl)oxy)prop-1-en-1-yl)-1,2-dimethoxybenzene, 5-(3-propoxyprop-1-en-1-yl)benzo[d][1,3]dioxole, 5-(3-butoxyprop-1-en-1-yl)benzo[d][1,3]dioxole, 5-(3-pentoxyprop-1-en-1-yl) benzo[d][1,3]dioxole, 5-(3-hexyloxyprop-1-en-1-yl)benzo[d][1,3]dioxole, 1-(3-(benzyloxy)prop-1-en-1-yl)-4-methylbenzene, 1-(3-(benzyloxy)prop-1-en-1-yl)-4-methoxybenzene, 2-(3-(benzyloxy)prop-1-en-1-yl)-1,3,5-trimethylbenzene, 1-(3-(benzyloxy)prop-1-en-1-yl)-4-(tert-butyl)benzene, 4-(3-(benzyloxy)prop-1-en-1-yl)-2-methoxyphenol, 4-(3-(benzyloxy)prop-1-en-1-yl)-2-methoxyphenol, 4-(3-(benzyloxy)prop-1-en-1-yl)-2,6-dimethoxyphenol, 2-methoxy-4-(((3-(3,4,5-trimethoxyphenyl)allyl)oxy)methyl)phenol, (E)-5-(3-(benzyloxy)prop-1-en-1-yl)benzo[d][1,3]dioxole, 5-(((3-(benzo[d][1,3]dioxol-5-yl)allyl)oxy)methyl) benzo[d][1,3]dioxole, 1-(3-(cinnamyloxy)prop-1-en-1-yl)-4-methoxybenzene, 4,4'-(oxybis(prop-1-ene-3,1-diyl))bis(methoxybenzene), 4-(3-(cinnamyloxy)prop-1-en-1-yl)-2-methoxyphenol, 5-(3-(cinnamyloxy)prop-1-en-1-yl)-1,2,3-trimethoxybenzene, capsiconiate, or dihydrocapsiconiate.

2. The compound as recited in claim 1 wherein $R^2$ is hydroxy located at the para position and a methoxy at the meta position and hydrogen at the remaining positions.

3. The compound as recited in claim 1 wherein at least one $R^2$ is selected from the group consisting of methyl, ethyl, propyl, isopropyl, butyl, isobutyl, and tert-butyl.

4. The compound as recited in claim 3 wherein at least one $R^2$ is selected from methyl, ethyl and tert-butyl and are located each independently at the meta and/or para positions with hydrogen at the remaining positions.

5. The compound as recited in claim 4 wherein $R^2$ is ethyl and is located at the para position with hydrogen at the remaining positions.

6. The compound as recited in claim 1 wherein one or two of the $R^2$ substituents are each independently selected from the group consisting of hydroxyl, methoxy, ethoxy, propoxy, isopropoxy and butoxy group, and $R^2$ is hydrogen at the remaining positions.

7. The compound as recited in claim 6 wherein a first $R^2$ is a methoxy located at the para and a second $R^2$ is a methoxy located at the meta position, and $R^2$ is hydrogen at the remaining positions.

8. The compound as recited in claim 1 wherein two $R^2$ groups, located at the para and meta positions, together form a methylenedioxy component of a ring with the carbon atoms to which they are attached.

9. A compound of Formula (I)

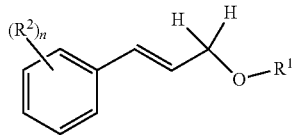

(I)

wherein $R^1$ represents a $C_3$ to $C_{20}$ optionally substituted linear, branched or cyclic alkyl; a $C_3$ to $C_{20}$ optionally substituted linear, branched or cyclic alkenyl; or a $C_3$ to $C_{20}$ optionally substituted linear, branched or cyclic alkynyl group, wherein a first $R^2$ is a hydroxy located at the para position; a second $R^2$ is a methoxy located at the meta position; and $R^2$ is hydrogen at the remaining positions, and wherein n is 5.

10. A method of releasing a fragrant compound from a precursor compound, wherein the fragrant compound is selected from the group consisting of a compound of Formula III (III)

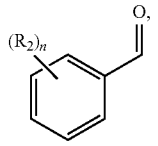

by exposing a precursor compound of Formula I:

(I)

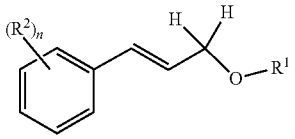

to an environment wherein the compound is oxidized [and wherein $R^1$ and $R^2$ are as set forth in claim 1.];

*wherein the compound of Formula I is capable of releasing upon oxidation an alcohol of formula $R^1OH$ selected from the group consisting of anisic alcohol, fenchylic alcohol, 9-decen-1-ol, phenethylol, citronellol, 3-methyl-5-phenyl-1-pentanol, (4-isopropylcyclohexyl)methanol, 4-phenylbutan-2-ol, 2,6-dimethyl-7-octen-2-ol, 3,7-dimethyl-2,6-octadien-1-ol, (Z)-3-hexen-1-ol, 2-hexanol, 5-ethyl-2-nonanol, 2,6-nonadien-1-ol, borneol, 1-octen-3-ol, 4-cyclohexyl-2-methyl-2-butanol, 2-methyl-4-phenyl-2-butanol, 2-methyl-1-phenyl-2-propanol, cyclomethylcitronellol, decanol, 8-p-menthanol, 3,7-dimethyl-1-octanol, 2,6-dimethyl-2-heptanol, dodecanol, tetrahydro-2-isobutyl-4-methyl-4(2H)-pyranol, linalool, 2-methoxy-4-propyl-1-cylohexanol, α-terpineol, tetrahydromuguol, 3,7-dimethyl-3-octanol, 5,6-dimethyl-1-methylethenylbicyclo[2.2.1]hept-5-ene-2-methanol, 2-phenyethanol, 1-phenylpropanol, 2-phenylpropanol, (2,5-dimethyl-2,3-dihydro-1H-inden-2-yl)methanol, 2,2-dimethyl-3-(3-methylphenyl)-propan-1-ol, 2-pentylcyclopentanol, 1,1-dimethyl-2-phenylethanol, 4-cyclohexyl-2-methylbutan-2-ol, menthol, 2,6-dimethylheptan-2-ol, 2-tert-butylcyclohexanol, 4-tert-butylcyclohexanol, 2,6-dimethyl-3,5-octadien-2-ol, 2-methyl-6-methylene-7-octen-2-ol, 3,7,9-trimethyl-1.6-decadien-3-ol, 3,6-dimethyloctan-3-ol, 1,2-dimethyl-3-prop-1-en-2-ylcyclopentan-1-ol, 2-methyl-4-phenylpentanol, 3-methyl-5-phenylpentanol, 3-methyl-5-(2,2,3-trimethyl-1-cyclopent-3-enyl)pentan-2-ol, (E)-3,3-dimethyl-5-(2,2,3-trimethyl-3-cyclopenten-1-yl)-4-penten-2-ol, 1-(2,2,6-trimethylcyclohexyl)hexan-3-ol, (E)-4-methyldec-3-en-5-ol, 4-(4-hydroxyphenyl)butan-2-ol, 4-(3-hydroxyprop-1-en-1-yl)-2-methoxyphenol, 4-(3-hydroxyprop-1-en-1-yl)-2-ethoxyphenol, 2,6-dimethyloctan-2-ol, 3,7-dimethylnon-1-en-3-ol, wherein:*

*a) the alcohol of formula $R^1OH$ is derived from the*

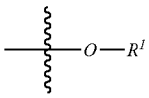

*moiety of the compound of Formula (I), such that $R^1$ moiety of the alcohol of formula $R^1OH$ corresponds to the $R^1$ moiety of the compound of Formula (I);*

*wherein each $R^2$ is, independently from each other at each position, hydrogen, hydroxyl group, an optionally substituted $C_1$-$C_6$ alkyl group, a $C_1$-$C_6$ alkoxy group, —O(C═O)$CH_3$ or—O(C═O)$CH(CH_3)_2$;*

*wherein $R^2$ may form an optionally substituted 5 or 6 membered ring;*

*wherein n=5 provided that $R^2$ is not hydrogen at every position; and*

*provided that Formula I is not 1-(3-isopropoxyprop-1-en-1-yl)-4-methylbenzene, 1-(3-isopropoxyprop-1-en-1-yl)-4-methoxybenzene, 1-butyl-4-(3-isopropoxyprop-1-en-1-yl)benzene, 1-(3-butoxyprop-1-en-1-yl)-4-methylbenzene, 1-(3-butoxyprop-1-en-1-yl)-3-methylbenzene, 2-(3-butoxyprop-1-en-1-yl)-1,3,5-trimethylbenzene, 1-(3-butoxyprop-1-en-1-y1)-4-(tert-butyl)benzene, 1-(3-butoxyprop-1-en-1-yl)-4-methoxybenzene, 1-(3-(tert-butoxy)prop-1-en-1-y1)-4-methylbenzene, 1-(3-(tertbutoxy) prop-1-en-1-y1)-4-methoxybenzene, 1-(3-(tert-butoxy)prop-1-en-1-yl)-4-butylbenzene, (E)-1-(3-((3,7-dimethyloct-6-en-1-yl)oxy)prop-1-en-1-y1)-4-methoxybenzene, 4-(3-((3,7-dimethyloct-6-en-1-yl)oxy)prop-1-en-1-y1)-1,2-dimethoxybenzene, 5-(3-propoxyprop-1-en-1-yl)benzo[d][1,3]dioxole, 5-(3-butoxyprop-1-en-1-yl)benzo[d][1,3]dioxole, 5-(3-pentoxyprop-1-en-1-yl) benzo[d][1,3]dioxole, 5-(3-hexyloxyprop-1-en-1-yl)benzo[d][1,3]dioxole, 1-(3-(benzyloxy)prop-1-en-1-yl)-4-methylbenzene, 1-(3-(benzyloxy)prop-1-en-1-yl)-4-methoxybenzene, 2-(3-(benzyloxy)prop-1-en-1-yl)-1,3,5-trimethylbenzene, 1-(3-(benzyloxy)prop-1-en-1-yl)-4-(tert-butyl)benzene, 4-(3-(benzyloxy)prop-1-en-1-y1)-2-methoxyphenol, 4-(3-(benzyloxy)prop-1-en-1-yl)-2-methoxyphenol, 4-(3-(benzyloxy)prop-1-en-1-yl)-2,6-dimethoxyphenol, 2-methoxy-4-(((3-(3,4,5-trimethoxyphenyl)allyl)oxy)methyl)phenol, (E)-5-(3-(benzyloxy)prop-1-en-1-yl)benzo[d][1,3]dioxole, 5-(((3-(benzo[d][1,3]dioxol-5-yl)allyl)oxy)methyl) benzo[d][1,3]dioxole, 1-(3-(cinnamyloxy)prop-1-en-1-yl)-4-methoxybenzene, 4,4'-(oxybis(prop-1-ene-3,1-diyl))bis(methoxybenzene), 4-(3-(cinnamyloxy)prop-1-en-1-yl)-2-methoxyphenol, 5-(3-(cinnamyloxy)prop-1-en-1-yl)-1,2,3-trimethoxybenzene, capsiconiate, or dihydrocapsiconiate.*

11. The method as recited in claim 10 wherein the method comprises the release of at least two compounds from the precursor compound wherein at least one of the compounds is a fragrant compound wherein the two compounds are the same or different and each independently comprises the formula (III):

(III)

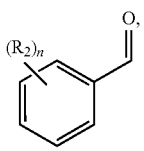

by exposing a precursor compound of Formula I:

(I)

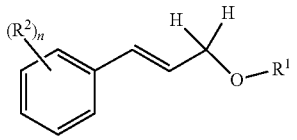

to an environment wherein the compound is oxidized.

12. The method as recited in claim 10 wherein $R^2$ is hydroxy located at the para position and a methoxy at the meta position and hydrogen at the remaining positions.

13. The method as recited in claim 10 wherein at least one $R^2$ is selected from the group consisting of methyl, ethyl, propyl, isopropyl, butyl, isobutyl, and tert-butyl.

14. The method as recited in claim 13 wherein at least one $R^2$ is selected from methyl, ethyl and tert-butyl and are located each independently at the meta and/or para positions with hydrogen at the remaining positions.

15. The method as recited in claim 14 wherein $R^2$ is ethyl and is located at the para position with hydrogen at the remaining positions.

16. The method as recited in claim 10 wherein one or two of the $R^2$ substituents comprises $C_1$-$C_6$ alkoxy groups selected from the group consisting of methoxy, ethoxy, propoxy, isopropoxy and butoxy group and $R^2$ is hydrogen at the remaining positions.

17. The method as recited in claim 16 wherein $R^2$ is a methoxy located at the para and meta position and $R^2$ is hydrogen at the remaining positions.

18. The method as recited in claim 17 wherein the alkoxy groups are located at the para and meta position and together form a methylenedioxy ring.

19. The method as recited in claim 10 wherein $R^2$ is a hydroxyl located at the para position and an ethoxy located at the meta position and $R^2$ is hydrogen at the remaining positions.

[20. The method as recited in claim 10 wherein $R^1$ is an optionally substituted linear, branched or cyclic $C_3$-$C_{20}$ alkyl.]

[21. The method as recited in claim 10 wherein $R^1$ is an optionally substituted linear, branched or cyclic $C_3$-$C_{20}$ alkenyl.]

[22. The method as recited in claim 10 wherein $R^1$ is an optionally substituted linear, branched or cyclic $C_3$-$C_{20}$ alkynyl.]

[23. The method as recited in claim 20 wherein $R^1$ is an optionally substituted linear, branched or cyclic $C_6$ to $C_{12}$ alkyl.]

[24. The method as recited in claim 21 wherein $R^1$ is an optionally substituted linear, branched or cyclic $C_6$ to $C_{12}$ alkenyl.]

[25. The method as recited in claim 22 wherein $R^1$ is an optionally substituted linear, branched or cyclic $C_6$ to $C_{12}$ alkynyl.]

26. The method as recited in claim 10 wherein the cyclic substituent *of the fragrant compound* comprises an oxygen in the ring *of Formula III*.

27. A compound of the following structure:

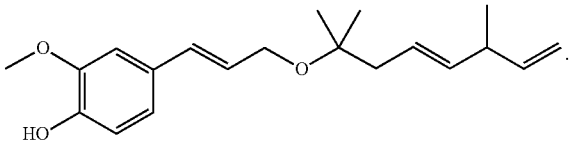

28. The compound as recited in claim 6 wherein the compound of Formula (I), upon oxidation, releases the alcohol of formula $R^1OH$ and a compound of formula (III)

(III)

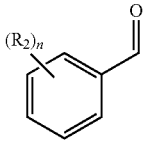

wherein one or two of the $R^2$ substituents are each independently selected from the group consisting of hydroxyl, methoxy, ethoxy, propoxy, isopropoxy and butoxy group, and $R^2$ is hydrogen at the remaining positions.

29. The compound as recited in claim 6 wherein a first $R^2$ is a methoxy located at the meta position, a second $R^2$ is a hydroxyl located at the para position, and $R^2$ is hydrogen at the remaining positions.

30. The compound as recited in claim 1 wherein the compound of Formula (I), upon oxidation, releases the alcohol of formula $R^1OH$ and a compound of formula (III):

(III)

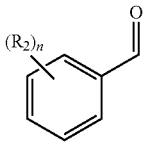

a) wherein each $R^2$ is, independently from each other at each position, hydrogen, hydroxyl group, an optionally substituted $C_1$-$C_6$ alkyl group, a $C_1$-$C_6$ alkoxy group, —O(C═O)$CH_3$ or —O(C═O)$CH(CH_3)_2$;

b) wherein $R^2$ may form an optionally substituted 5 or 6 membered ring; and c) wherein n=5 provided that $R^2$ is not hydrogen at every position.

*31. The compound as recited in claim 1 wherein the compound is (E)-4-(3-((2,6-dimethyloctan-2-yl)oxy)prop-1-en-1-y1)-2-methoxyphenol or (E)-4-(3-((2,6-dimethyloctan-2-yl)oxy)prop-1-en-1-yl)-1,2-dimethoxybenzene.*

*32. The compound as recited in claim 9 wherein the compound is (E)-4-(3-((2,6-dimethyloctan-2-yl)oxy)prop-1-en-1-y1)-2-methoxyphenol.*

*33. The compound as recited in claim 9 wherein said compound is capable of releasing upon oxidation an alcohol of formula $R^1OH$ wherein:*

*the alcohol of formula $R^1OH$ is derived from the*

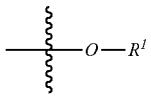

*moiety of the compound of Formula (I), such that the $R^1$ moiety of the alcohol of formula $R^1OH$ corresponds to the $R^1$ moiety of the compound of Formula (I).*

*34. The method as recited in claim 10 wherein the precursor compound of Formula I is (E)-4-(3-((2,6-dimeth-*

*yloctan-2-yl)oxy)prop-1-en-1-yl)-2-methoxyphenol or (E)-4-(3-((2,6-dimethyloctan-2-yl)oxy)prop-1-en-1-yl)-1,2-dimethoxybenzene.*

*35. The method as recited in claim 11 wherein the precursor compound of Formula I is (E)-4-(3-((2,6-dimethyloctan-2-yl)oxy)prop-1-en-1-yl)-2-methoxyphenol or (E)-4-(3-((2,6-dimethyloctan-2-yl)oxy)prop-1-en-1-yl)-1,2-dimethoxybenzene.*

*36. The compound as recited in claim 30 wherein the compound of Formula (I) is (E)-4-(3-((2,6-dimethyloctan-2-yl)oxy)prop-1-en-1-yl)-2-methoxyphenol or (E)-4-(3-((2,6-dimethyloctan-2-yl)oxy)prop-1-en-1-yl)-1,2-dimethoxybenzene.*

* * * * *